United States Patent
Dillon et al.

(10) Patent No.: US 10,716,693 B2
(45) Date of Patent: Jul. 21, 2020

(54) STENT DEPLOYMENT SYSTEM WITH OVERMOLDED TIP

(71) Applicant: Cook Medical Technologies LLC, Bloomington, IN (US)

(72) Inventors: Conor Dillon, Tipperary (IE); William Riordan, Limerick (IE)

(73) Assignee: Cook Medical Technologies LLC, Bloomington, IN (US)

(*) Notice: Subject to any disclaimer, the term of this patent is extended or adjusted under 35 U.S.C. 154(b) by 72 days.

(21) Appl. No.: 16/059,636

(22) Filed: Aug. 9, 2018

(65) Prior Publication Data
US 2018/0344496 A1    Dec. 6, 2018

Related U.S. Application Data (62) Division of application No. 14/934,859, filed on Nov. 6, 2015, now Pat. No. 10,076,435.
(Continued)

(51) Int. Cl.
*A61F 2/966* (2013.01)
*A61M 25/00* (2006.01)
(Continued)

(52) U.S. Cl.
CPC .......... *A61F 2/966* (2013.01); *A61M 25/001* (2013.01); *A61M 25/0009* (2013.01);
(Continued)

(58) Field of Classification Search
CPC ............ A61M 25/001; A61M 25/0054; A61M 25/0068; A61M 25/0074;
(Continued)

(56) References Cited

U.S. PATENT DOCUMENTS 4,753,765 A    6/1988 Pande
5,240,537 A    8/1993 Bodicky
(Continued)

FOREIGN PATENT DOCUMENTS

EP    0950425 A2    10/1999

OTHER PUBLICATIONS

European Patent Office, Intention to Grant for Application No. 16150459.2-1113, dated Jun. 22, 2018, Applicant: Cook Medical Technologies LLC, Netherlands.
(Continued)

*Primary Examiner* — Matthew P Travers
(74) *Attorney, Agent, or Firm* — Liell & McNeil (57) ABSTRACT

A deployment system for a self expanding stent includes a catheter assembly with a tip attached to a distal end segment of an elongate tube. The tip includes a proximal portion molecularly joined to a distal portion, which has a lower durometer hardness than the proximal portion. The proximal portion includes an anchor surface in contact with the distal portion, and oriented perpendicular to a central axis of the elongate tube. The elongate tube may be formed from a thermosetting polyimide, and the overmolded tip may be made from two different colored and different hardnesses of polyether block amide material. The tip is overmolded onto an untreated external surface of the elongate tube.

19 Claims, 5 Drawing Sheets

Related U.S. Application Data (60) Provisional application No. 62/120,558, filed on Feb. 25, 2015.

(51) Int. Cl.
    *B29C 45/16*      (2006.01)
    *B29C 45/14*      (2006.01)
    *B29L 31/00*      (2006.01)

(52) U.S. Cl.
CPC . *A61M 25/0054* (2013.01); *A61M 2025/0008* (2013.01); *A61M 2025/0081* (2013.01); *A61M 2207/00* (2013.01); *B29C 45/14344* (2013.01); *B29C 2045/1659* (2013.01); *B29L 2031/7542* (2013.01)

(58) Field of Classification Search
CPC ............... A61M 25/008–2025/0081; A61M 2025/0008; A61M 25/0009; A61M 2207/00; A61F 2/966; B29L 2031/7542; B29C 45/0062; B29C 45/14336; B29C 45/14344; B29C 2045/1436; B29C 2045/14368; B29C 45/14614; B29C 2045/1659; B29C 45/1676; B29C 2045/1681
See application file for complete search history.

(56) References Cited

U.S. PATENT DOCUMENTS

| | | |
|---|---|---|
| 5,762,637 A | 6/1998 | Berg et al. |
| 5,772,641 A | 6/1998 | Wilson |
| 6,068,635 A | 5/2000 | Gianotti |
| 6,149,996 A | 11/2000 | Helgerson et al. |
| 7,758,624 B2 | 7/2010 | Dorn et al. |
| 2002/0183826 A1 | 12/2002 | Dorn et al. |
| 2007/0118201 A1 | 5/2007 | Pappas et al. |
| 2013/0012924 A1 | 1/2013 | Davis et al. |
| 2014/0142542 A1 | 5/2014 | Rosenbaum et al. |
| 2014/0148889 A1* | 5/2014 | Deshmukh ............ A61F 2/962 623/1.11 |

OTHER PUBLICATIONS

Mathys & Squire Intellectual Property, Response to EP Office Action, European Patent Application No. 16150459.2, dated Aug. 23, 2017, London.

European Patent Office, EP Office Action, Application No. 16150459.2-1651, dated Apr. 25, 2017, Applicant: Cook Medical Technologies LLC, Netherlands.

* cited by examiner

STENT DEPLOYMENT SYSTEM WITH OVERMOLDED TIP

TECHNICAL FIELD

The present disclosure relates generally to deployment systems for self expanding stents, and more particularly to an overmolded tip for a catheter assembly of a stent deployment system.

BACKGROUND

Deployment of self expanding stents has traditionally been performed using known pin and pull systems. More recently, the industry has looked toward one handed deployment strategies to replace the two handed pin and pull systems. One such strategy involves the use of a thumbwheel design in which deployment of the stent occurs responsive to rotation of the thumbwheel. In either deployment system, a retractable sheath holds the stent in a compressed state until the stent is positioned at a desired deployment location within a patient. Thereafter, the retractable sheath is slid in a proximal direction to uncover the stent and allow the same to expand at the deployment site.

In addition to a retractable sheath, deployment systems for self expanding stents utilize an underlying catheter assembly that includes a distal segment with a soft tip attached thereto that is a larger diameter than the underlying catheter. The stent is compressed around a carrier segment of the catheter assembly when the deployment system is in a pre-deployment configuration. One current strategy for attaching the pliable distal tip to the catheter involves application of two types of glue in precise quantities and shaped by a skilled manufacturing technician. While this strategy has performed well, the catheter assembly can be relative expensive since each catheter assembly must essentially be hand made by a highly skilled manufacturing technician.

The present disclosure is directed toward one or more of the problems set forth above.

SUMMARY

In one aspect, a stent deployment system includes a catheter assembly comprised of a tip attached to, and extending distally beyond, a distal end segment of an elongate tube. A self expanding stent is compressed around a carrier segment of the elongate tube. A retractable sheath is mounted on the catheter assembly, and is movable along a central axis of the elongate tube between a pre-deployment configuration at which the expandable stent and the carrier segment are covered, and a post-deployment configuration at which the expandable stent is uncovered and a distal end of the retractable sheath is located proximally of the carrier segment. The distal end segment of the elongate tube has an untreated external surface along an entire length of the distal end segment. The tip includes a proximal portion molecularly joined to a distal portion, which has a lower durometer hardness than the proximal portion. The proximal portion includes an anchor surface in contact with the distal portion and oriented perpendicular to the central axis of the elongate tube.

In another aspect, a method of making a stent deployment system includes overmolding a tip of polyether block amide on an untreated external surface of a distal end segment of an elongate tube of thermosetting polyimide. The overmolding step includes molding a proximal portion of the tip with a first polyether block amide material, and then molding a distal portion of the tip with a second polyether block amide, which has a lower durometer hardness when solidified than the first polyether block amide material. The step of molding the proximal portion includes forming an anchor surface that is oriented perpendicular to a central axis of the elongate tube. The step of molding the distal portion includes contacting the anchor surface of the proximal portion, and molecularly joining the distal portion to the proximal portion. A self expanding stent is compressed around a carrier segment of the elongate tube. A retractable sheath is mounted on the catheter assembly in a pre-deployment configuration at which the expandable stent and the carrier segment are covered by the retractable sheath.

DETAILED DESCRIPTION

Figure 1:
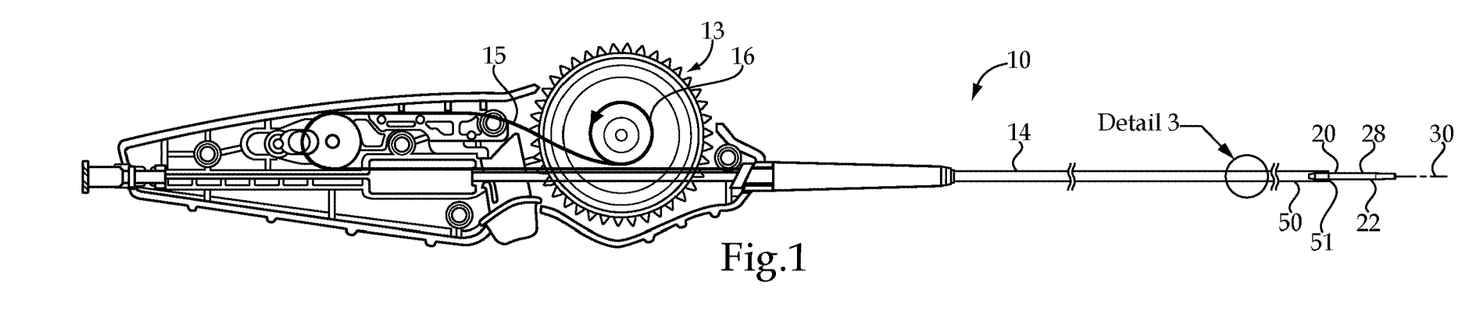
FIG. 1 is a side schematic view of a stent deployment system according to the present disclosure.
Figure 2:
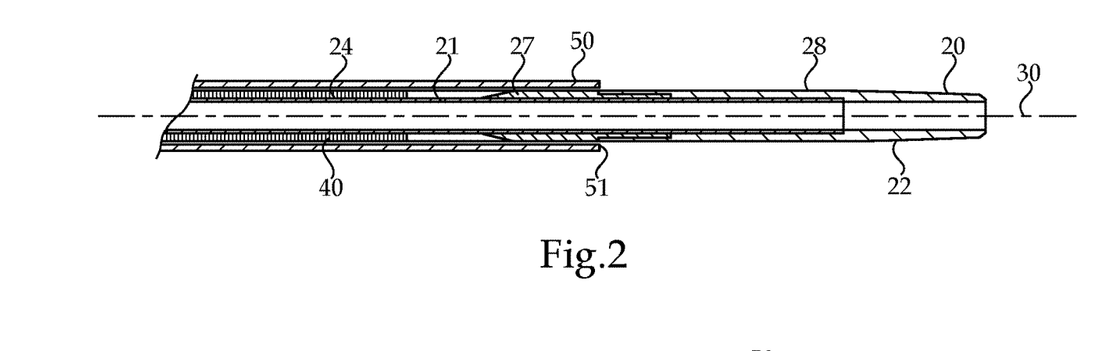
FIG. 2 is a sectioned view of a distal portion (detail 2) of the stent deployment system of FIG. 1.
Figure 3:
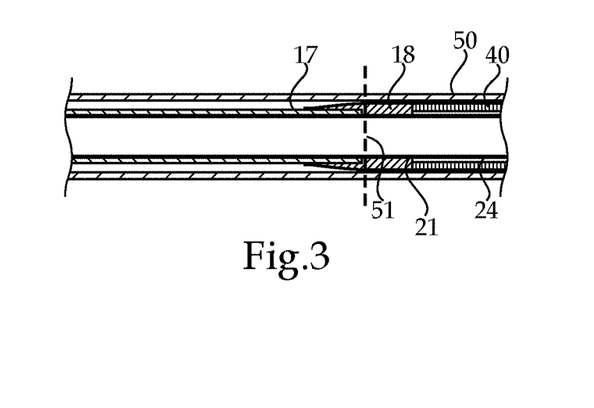
FIG. 3 is a sectioned view of detail 3 of the stent deployment system of FIG. 1.

Referring initially to FIGS. 1-3, a stent deployment system 10 includes a catheter assembly 20 that includes an elongate tube 21 with a tip 22 attached to, and extending distally beyond, a distal end segment 23 of the elongate tube 21. Tip 22 generally has a larger outside diameter than an outside diameter of elongate tube 21. A self expanding stent 40 is compressed around a carrier segment 24 of the elongate tube 21. A retractable sheath 50 is mounted on the catheter assembly, and is movable along a central axis 30 of the elongate tube 21 between a pre-deployment configuration (as shown) and a post-deployment configuration. The self expanding stent 40 and the carrier segment 23 are covered by the retractable sheath 50 in the pre-deployment configuration. The self expanding stent 40 is un-covered, and a distal end 51 of the retractable sheath 50 is located proximally of the carrier segment 23, in the post-deployment configuration. In the illustrated embodiment, the stent deployment system 10 utilizes a thumbwheel assembly 13 in order to move retractable sheath 50 between its pre-deployment configuration, as shown, and the post-deployment configuration. Stent deployment system 10 may include an outer sheath 14, that has an internal lumen sized to receive retractable sheath 50 and catheter assembly 20, including tip 22. A pull 15 has a proximal end wound onto spool 16 and a distal end attached to retractable sheath 50. In this way, retractable sheath 50 moves from the pre-deployment configuration to the post-deployment configuration responsive to rotation of the thumbwheel of the thumbwheel assembly 13 to wind pull 15 onto spool 16. The stent deployment system 10 may also include a pusher catheter 17 with a pusher band 18 mounted on its distal end to maintain self expanding stent 40 at a desired location along central axis 30 when retractable sheath 50 is being slid from the pre-deployment configuration to the post-deployment configuration. Although the stent deployment system 10 is shown utilizing a thumbwheel assembly 13, those skilled in the art will appreciate that a conventional pin and pull structure for maneuvering retractable sheath 50 would also fall within the intended scope of the present disclosure. Stent deployment system 10 has structure similar to stent deployment systems well known in the art, with the exception of the structure of tip 22, and the overall structure of catheter assembly 20 in general.

Figure 4:
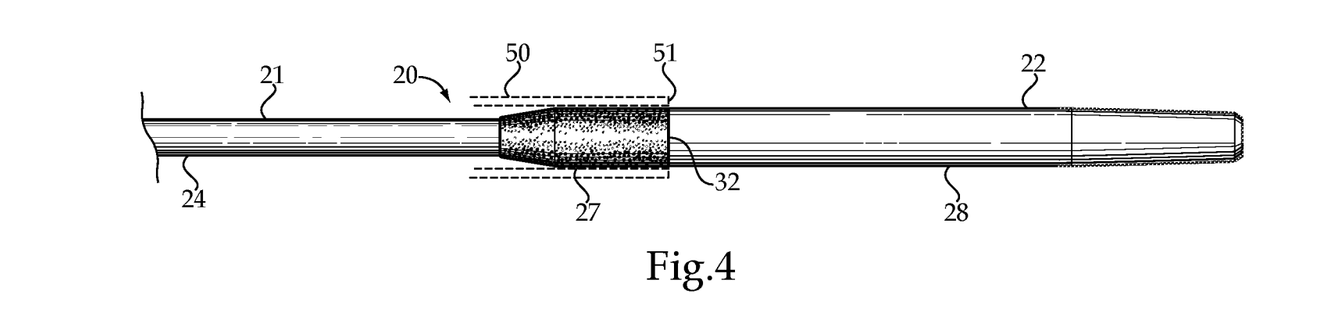
FIG. 4 is a side view of a distal portion of the catheter assembly from the stent deployment system of FIG. 1.
Figure 5:
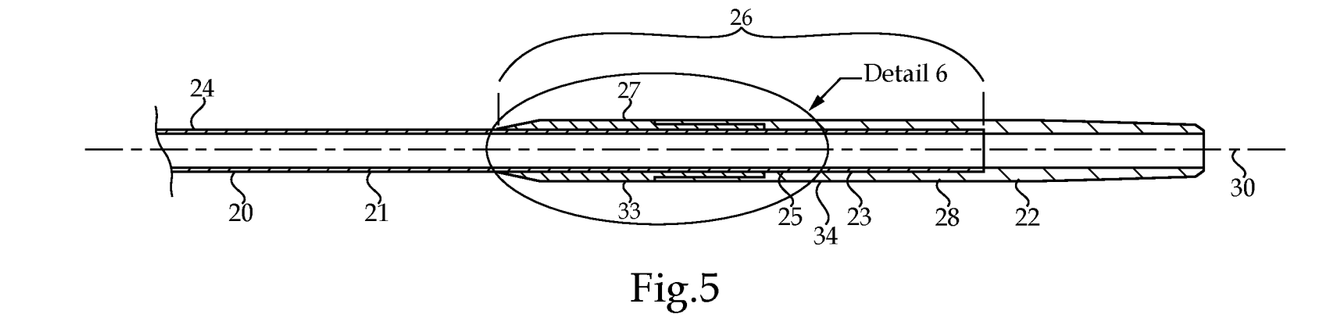
FIG. 5 is a sectioned view of the catheter assembly portion shown in FIG. 4.
Figure 6:
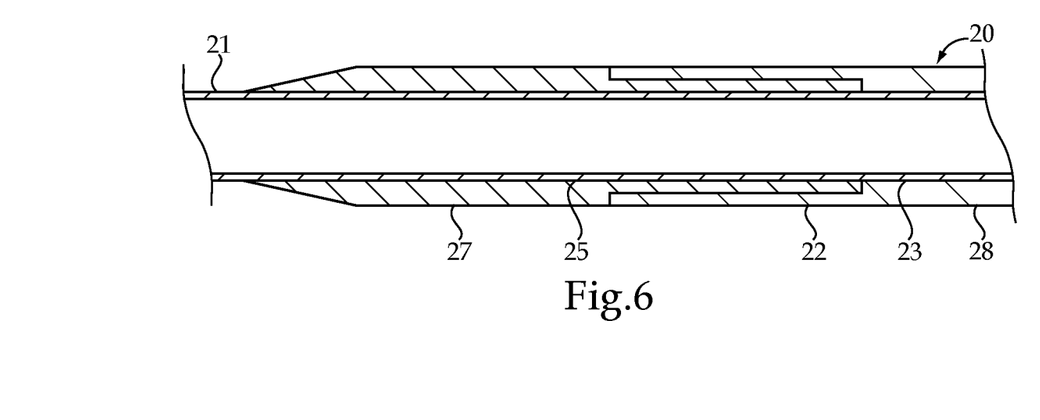
FIG. 6 is an enlarged sectioned view of detail 6 from FIG. 5.
Figure 7:
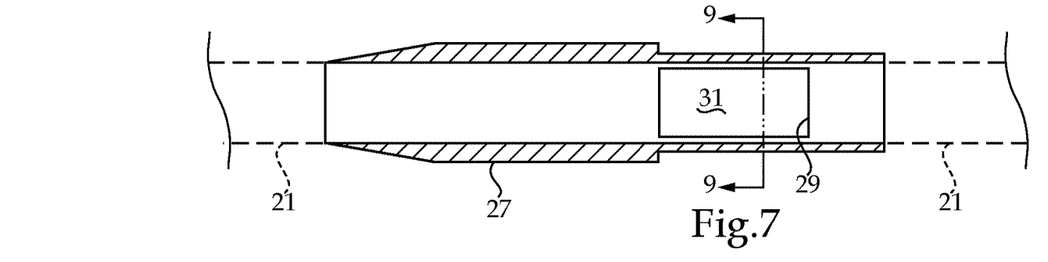
FIG. 7 is a sectioned view through the proximal portion of the tip for the catheter assembly of FIG. 4.
Figures 8, 10, 11:
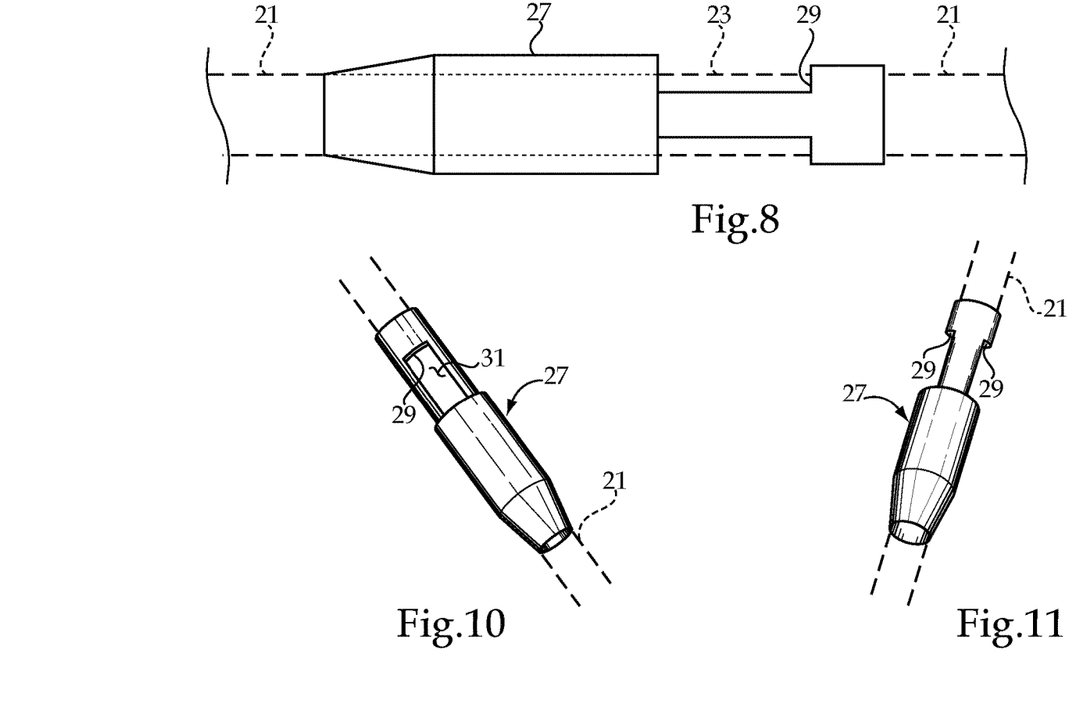
FIG. 8 is a side view of the proximal portion of the tip.
FIG. 10 is an isometric view of the proximal portion of the tip.
FIG. 11 is another isometric view of the proximal portion of the tip.
Figure 9:
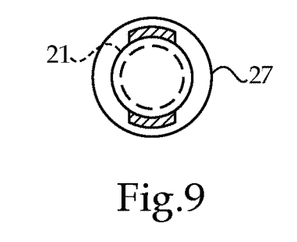
FIG. 9 is a sectioned view of the proximal portion of the tip as viewed along sectioned lines 9-9 of FIG. 7.

Referring in addition to FIGS. 4-6 the elongate tube 21 of catheter assembly 20 may be formed from a suitable thermosetting polyimide in order to facilitate overmolding a tip 22 of polyether block amide. Unlike prior art structures, the distal end segment 23 of the elongate tube 21 has an untreated external surface 25 along an entire length 26 of the distal end segment 23. The phrase "untreated external surface" means that the external surface 25 has not been manipulated or changed in any way to facilitate attachment of tip 22. Thus, the untreated external surface 25 has no flange on its distal end, and includes no texturing or other surface features that are anything but parallel with central axis 30 such that the external surface 25 is identical to the external surface of carrier segment 24 and maybe all of the remaining portions of the elongate tube 21 away from distal end segment 23. The tip 22 includes a proximal portion 27 that is molecularly joined to a distal portion 28, which has a lower durometer hardness than the proximal portion 27. The term "molecularly joined" means that the proximal portion 27 and the distal portion 28 are molded from the same or sufficiently similar plastic materials that the proximal portion 27 and the distal portion 28 intermix with each other at their interface during the molding process of tip 22, before the entire tip 22 has solidified. The underlying elongate tube 21 remains solid during the entire two shot molding process of tip 22.

Figure 12:
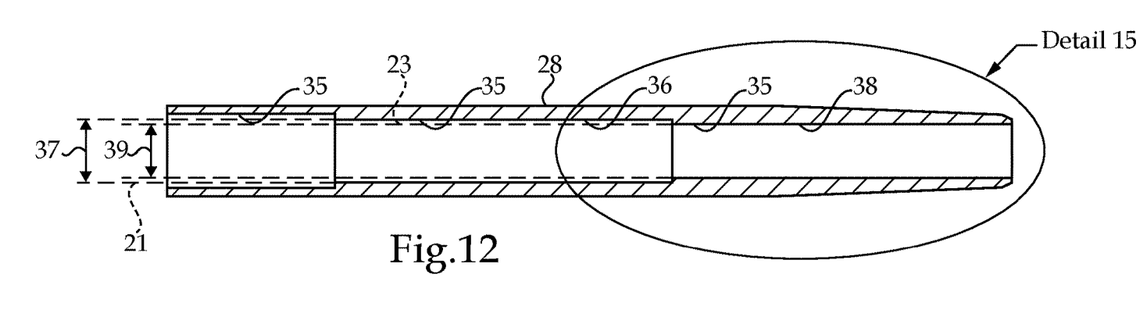
FIG. 12 is a side sectioned view of the distal portion of the tip for the catheter assembly of FIG. 4.
Figure 13:
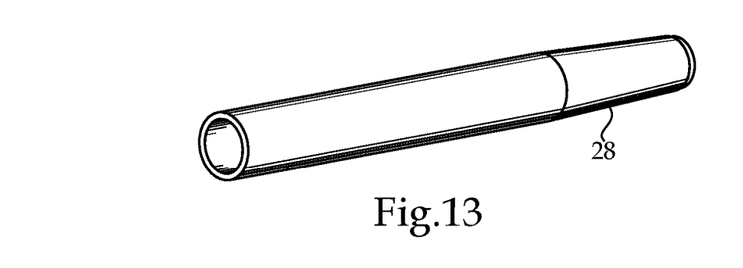
FIG. 13 is an isometric view of the distal portion of the tip.
Figure 14:
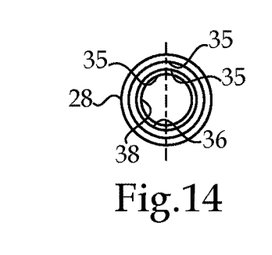
FIG. 14 is an end view of the distal portion of the tip.
Figure 15:
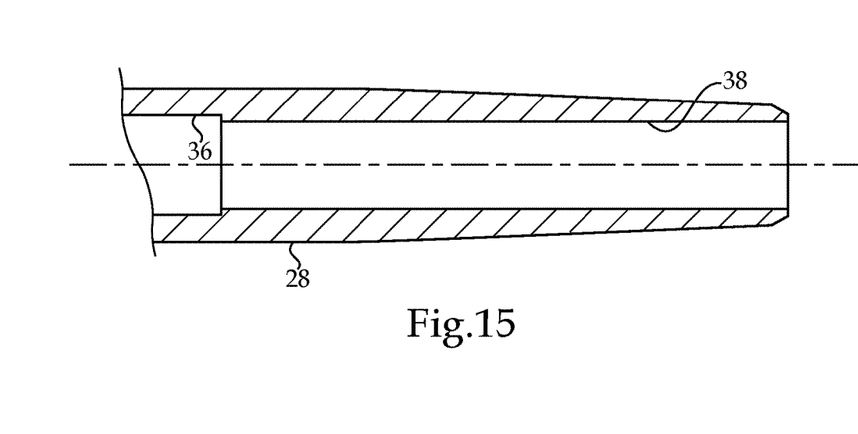
FIG. 15 is an enlarged sectioned view of an end of the distal portion of the tip and identified as detail 15 in FIG. 12.

Referring now in addition to FIGS. 7-13, the proximal portion 27 includes an anchor surface 29 in contact with the distal portion 28, and oriented perpendicular to the central axis 30 of the elongate tube 21. Although not necessary, distal portion 28 of the tip 22 may be in contact with the elongate tube 21 through a window 31 defined by the proximal portion 27. Thus, in the illustrated embodiment, the tip 22 maintains attachment to elongate tube 21 without reliance upon anchoring features textured into or formed on the elongate tube 21, as in the prior art. Thus, the untreated external surface 25 has no anchoring features, which are surfaces oriented at an angle greater than zero with respect to the centerline 30. Although not necessary, the proximal portion 27 may be shorter than the distal portion 28 along central axis 30. In the illustrated embodiment, proximal portion 27 includes a pair of anchor surfaces 29 that are located on opposite sides of central axis 30, as best shown in FIGS. 7-11. Although not necessary, proximal portion 27 may include a uniform diameter segment 33 that has a same diameter as a uniform diameter segment 34 of the distal portion 28. As best shown in FIG. 12, the distal portion 28 of tip 22 may define three consecutive segments 35 that each define different internal diameters. One of the internal diameters 36 matches an outside diameter 37 of the elongate tube 21, and another one of the internal diameters 38 matches an internal diameter 39 of the elongate tube 21. These features may help to avoid discontinuities between the distal end of the elongate tube 21 and the corresponding features of tip 22.

Although not necessary, proximal portion 27 and distal portion 28 may be formed from different colors of a suitable plastic material, such as polyether block amide, so that the proximal portion 27 visibly contrasts with the distal portion 28 to define a contrast line 32 that encircles the central axis 30, as best shown in FIG. 4. When the stent deployment system 10 is in the pre-deployment configuration, as shown, the distal end 51 of retractable sheath 50 and the contrast line 32 may have corresponding positions along the central axis 30. Thus, the contrast line 32 can be utilized at the time of manufacture to correctly set the corresponding relative positions of the retractable sheath relative to the catheter assembly 20 in the pre-deployment configuration. Although not necessary, the contrast line 32 may be located proximal to the anchor surface(s) 29 along central axis 30.

INDUSTRIAL APPLICABILITY

The stent deployment system 10 of the present disclosure is generally applicable to the delivery of self expanding stents. This disclosure is specifically applicable to the construction of a catheter assembly 20 that includes an elongate tube 21 with an overmolded tip 22.

Figure 16:
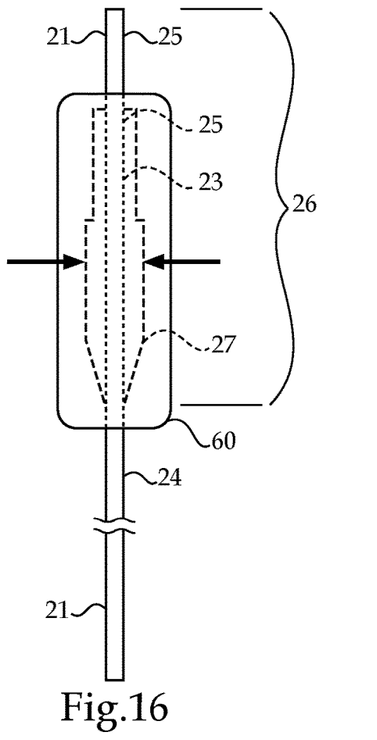
FIG. 16 is a side schematic view of the molding process for the proximal portion of the tip.
Figure 17:
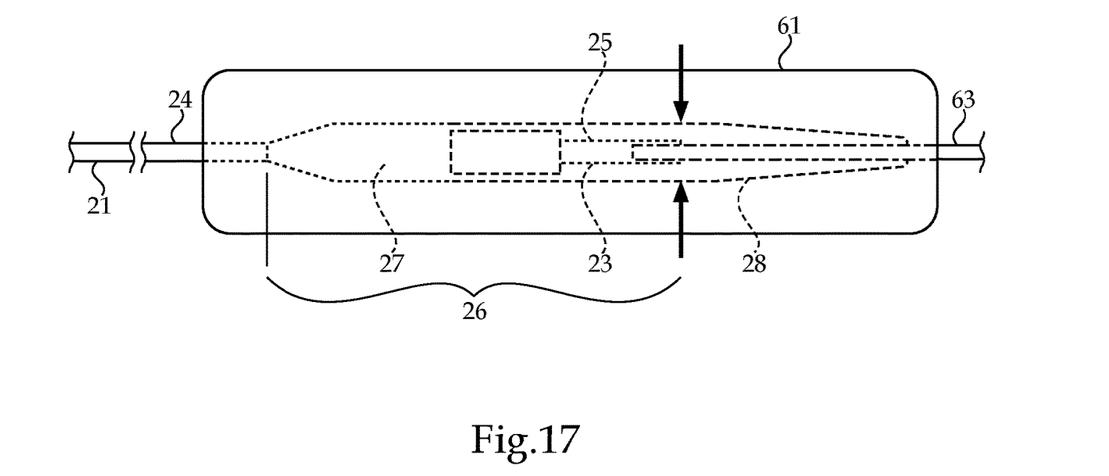
FIG. 17 is side schematic view of the molding process for the distal portion of the tip.

One method of making the stent deployment system 10 includes overmolding tip 22 of polyether block amide on an untreated external surface 25 of a distal end segment 23 of an elongate tube 21 of thermosetting polyimide. Those skilled in the art will appreciate that other known materials with similar characteristics and behaviors may be substituted in place of the thermosetting polyimide and polyether block amide identified with respect to the illustrated embodiment. The tip 22 may be molded in two steps as illustrated in FIGS. 16 and 17. In particular, the step of overmolding tip 22 includes molding the proximal portion 27 of tip 22 with a first polyether block amide material, and then molding the distal portion 28 of tip 22 with a second polyether block amide. The second polyether block amide has a lower durometer hardness when solidified that the first polyether block amide material, and may be of a different color to facilitate formation of the contrast line 32 discussed earlier. FIG. 16 is useful for showing the proximal portion 27 being overmolded onto the distal end segment 23 of elongate tube 21 when a mold 60 is oriented in a vertical orientation. Thus, the elongate tube 21 functions as a core in first mold 60. The arrows in FIG. 16 show that the material used for forming proximal portion 27 may enter mold 60 through two gates. Nevertheless, any number of gates could be used in the injection molding process. After removal from mold 60, the piece may be inspected and any flash or excess material removed along mold lines or the like in a manner well known in the art. The distal portion 28 is then overmolded onto proximal portion 27, a mandrel core 63 and elongate tube 21 with a second mold 61, which may be oriented in a horizontal orientation as shown in FIG. 17. Thus, the elongate tube 21 and the proximal portion 27 act as cores in the second mold 61. The molding of proximal portion 27 includes forming an anchor surface(s) 29 that is oriented perpendicular to the central axis 30 of elongate tube 21. The molding of the distal portion 28, which is performed after proximal portion 27 has solidified, includes contacting the distal portion 28 with the anchor surface(s) 29 of proximal portion 27, and molecularly joining the distal portion 28 to the proximal portion 27 at their interface. The molecular joining is facilitated by the molten material for distal portion 28 melting contact surfaces of proximal portion 27 prior distal portion solidifying. After removal from mold 61, mandrel core 63 is removed and any excess material from mold joints and/or gates may be removed in a manner well known in the art.

After constructing catheter assembly 20, a self expanding stent 40 is compressed and loaded into a retractable sheath 50. Later in the assembly catheter assembly 20 is back loaded into retractable sheath 50 and through self expanding stent 40 to a pre-deployment configuration at which the expandable stent 40 and the carrier segment 24 are covered by the retractable sheath 50.

Referring again specifically to FIGS. 16 and 17, the arrows are used to indicate the injection molding process and possible gate locations at which the polyether block amide material might be injected into the respective molds 60 and 61. Although not necessary, the step of molding the distal portion 28 may include moving the second polyether block amide into contact with the elongate tube 21 through a window 31 defined by the proximal portion 27. By utilizing differing colors in the first and second polyether block amide materials, a visible contract line 32 is made on the tip 22 that encircles the central axis 30. The contrast line 32 may assist manufacturing personnel by providing a visible location to enable the distal end 51 of the retractable sheath to be positioned at a corresponding position along central axis 30 with the contrast line 32. As stated earlier, the contrast line 32 may be located during the molding process to be proximal to the anchor surface(s) 29 along central axis 30. Likewise, the proximal portion 27 may be sized to be shorter than the distal portion 28 along central axis 30. Also as stated earlier, the proximal portion 27 may be shaped to have a uniform diameter segment 33 that has a same diameter has a uniform diameter segment 34 of distal portion 28.

The overmolding strategy of the present disclosure provides several advantages. First, the elongate tube 21 need not be processed to include anchor features such as flanges or external texturing in order to facilitate attachment to an overmolded tip 22. Furthermore, by utilizing a two step process in overmolding tip 22, the distal portion 28 can utilize a lower durometer hardness than the proximal portion 27 in order to provide texture and flexibility that physicians have come to recognize and expect. Finally, by utilizing the two shot injection overmolding strategy of the present disclosure, the catheter assemblies can be made more uniform in the manufacturing process with less reliance upon custom handmade tips associated with catheter assemblies of the past.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A method of making a stent deployment system, comprising the steps of:
    overmolding a tip of polyether block amide on an untreated external surface of a distal end segment of an elongate tube of thermosetting polyimide;
    wherein the overmolding step includes molding a proximal portion of the tip with a first polyether block amide material in contact with the untreated external surface, and then molding a distal portion of the tip with a second polyether block amide, which has a lower durometer hardness when solidified than the first polyether block amide material;
    wherein the step of molding the proximal portion includes forming an anchor surface that is oriented perpendicular to a central axis of the elongate tube;
    wherein the step of molding the distal portion includes contacting the distal portion with the anchor surface of the proximal portion, contacting the distal portion with the untreated external surface, and molecularly joining the distal portion to the proximal portion;
    compressing a self expanding stent around a carrier segment of the elongate tube;
    mounting a retractable sheath on the elongate tube in a pre-deployment configuration at which the self expanding stent and the carrier segment are covered by the retractable sheath.

2. The method of claim 1 including a step of making a visible contrast line on the tip that encircles the central axis in a plane perpendicular to the central axis by using contrasting colors in the first and second polyether block amides.

3. The method of claim 2 including positioning a distal end of the retractable sheath and the contrast line at corresponding positions along the central axis.

4. The method of claim 3 wherein the step of molding the distal portion includes moving the second polyether block amide into contact with the elongate tube through a window defined by the proximal portion.

5. The method of claim 4 including locating the contrast line proximal to the anchor surface along the central axis.

6. The method of claim 5 including sizing the proximal portion of the tip to be shorter than the distal portion of the tip.

7. The method of claim 6 including shaping the proximal portion to have a uniform diameter segment with a same diameter as a uniform diameter segment of the distal portion.

8. The method of claim 1 wherein the anchor surface faces in a proximal direction.

9. A method of making a stent deployment system, comprising the steps of:
    overmolding a tip of polyether block amide on an untreated external surface of a distal end segment of an elongate tube of thermosetting polyimide:
    wherein the overmolding step includes molding a proximal portion of the tip with a first polyether block amide material, and then molding a distal portion of the tip with a second polyether block amide, which has a lower durometer hardness when solidified than the first polyether block amide material;
    wherein the step of molding the proximal portion includes forming an anchor surface that is oriented perpendicular to a central axis of the elongate tube;
    wherein the step of molding the distal portion includes contacting the distal portion with the anchor surface of the proximal portion, and molecularly joining the distal portion to the proximal portion;

compressing a self expanding stent around a carrier segment of the elongate tube;

mounting a retractable sheath on the elongate tube in a pre-deployment configuration at which the self expanding stent and the carrier segment are covered by the retractable sheath; and wherein the step of molding the distal portion includes moving the second polyether block amide into contact with the elongate tube through a window defined by the proximal portion.

10. A method of making a catheter assembly, comprising the steps of:

overmolding a tip of polyether block amide on an untreated external surface of a distal end segment of an elongate tube of thermosetting polyimide;

wherein the overmolding step includes molding a proximal portion of the tip with a first polyether block amide material in contact with the untreated external surface, and then molding a distal portion of the tip with a second polyether block amide, which has a lower durometer hardness when solidified than the first polyether block amide material;

wherein the step of molding the proximal portion includes forming an anchor surface that faces in a proximal direction; and wherein the step of molding the distal portion includes contacting the distal portion with the anchor surface of the proximal portion, contacting the distal portion with the untreated external surface, and molecularly joining the distal portion to the proximal portion.

11. The method of claim 10 wherein at least a portion of the anchor surface is oriented perpendicular to a central axis of the elongate tube.

12. The method of claim 10 wherein the step of molding the distal portion includes moving the second polyether block amide into contact with the elongate tube through a window defined by the proximal portion.

13. The method of claim 10 including a step of making a visible contrast line on the tip that encircles a central axis of the elongate tube in a plane perpendicular to the central axis by using contrasting colors in the first and second polyether block amides.

14. The method of claim 13 wherein the step of molding the distal portion includes moving the second polyether block amide into contact with the elongate tube through a window defined by the proximal portion.

15. The method of claim 14 including locating the contrast line proximal to the anchor surface along the central axis.

16. The method of claim 15 including sizing the proximal portion of the tip to be shorter than the distal portion of the tip.

17. The method of claim 16 including shaping the proximal portion to have a uniform diameter segment with a same diameter as a uniform diameter segment of the distal portion.

18. A method of making a catheter assembly, comprising the steps of:

overmolding a tip of polyether block amide on an untreated external surface of a distal end segment of an elongate tube of thermosetting polyimide;

wherein the overmolding step includes molding a proximal portion of the tip with a first polyether block amide material, and then molding a distal portion of the tip with a second polyether block amide, which has a lower durometer hardness when solidified than the first polyether block amide material;

wherein the step of molding the proximal portion includes forming an anchor surface that faces in a proximal direction; and wherein the step of molding the distal portion includes contacting the distal portion with the anchor surface of the proximal portion, and molecularly joining the distal portion to the proximal portion; and wherein the distal portion includes an internal diameter segment that matches an internal diameter of the elongate tube.

19. The method of claim 18 wherein the internal diameter segment is a first internal diameter segment; and the distal portion includes a second internal diameter segment that matches an external diameter of the elongate tube.

\* \* \* \* \*